US012636337B2

(12) United States Patent
Cho

(10) Patent No.: US 12,636,337 B2
(45) Date of Patent: *May 26, 2026

(54) COMPOSITION FOR ANTI-INFLAMMATION, WOUND HEALING OR WOUND HEALING PROMOTION, COMPRISING ROSE STEM CELL-DERIVED EXOSOMES AS ACTIVE INGREDIENT

(71) Applicant: EXOCOBIO INC., Seoul (KR)

(72) Inventor: Byong Seung Cho, Gunpo-si Gyeonggi-do (KR)

(73) Assignee: EXOCOBIO INC., Seoul (KR)

( * ) Notice: Subject to any disclaimer, the term of this patent is extended or adjusted under 35 U.S.C. 154(b) by 622 days.

This patent is subject to a terminal disclaimer.

(21) Appl. No.: 17/993,789

(22) Filed: Nov. 23, 2022

(65) Prior Publication Data

US 2023/0093110 A1 Mar. 23, 2023

Related U.S. Application Data

(63) Continuation of application No. PCT/KR2021/006189, filed on May 18, 2021.

(30) Foreign Application Priority Data

Jun. 4, 2020 (KR) ........................ 10-2020-0067466
Mar. 16, 2021 (KR) ........................ 10-2021-0034311

(51) Int. Cl.
*A61K 36/738* (2006.01)
*A61P 29/00* (2006.01)
(52) U.S. Cl.
CPC ............ *A61K 36/738* (2013.01); *A61P 29/00* (2018.01)

(58) Field of Classification Search
None
See application file for complete search history.

(56) References Cited

U.S. PATENT DOCUMENTS 11,690,797 B2 * 7/2023 Yi ........................ A61K 8/0212
424/401
2017/0209365 A1 7/2017 Cho et al.
2021/0121393 A1 4/2021 Yi et al.

FOREIGN PATENT DOCUMENTS

| CN | 109568414 A | 4/2019 |
| KR | 10-2012-0135550 A | 12/2012 |
| KR | 10-2016-0086253 A | 7/2016 |
| KR | 10-2019-0050286 A | 5/2019 |
| KR | 10-1998032 B1 | 7/2019 |
| KR | 10-2058444 B1 | 12/2019 |

(Continued)

OTHER PUBLICATIONS

Fabi et al. the potential of topical and injectable growth factors and cytokines for skin rejuvenation. Facial Plastic Surgery, 2014. vol .30:2, p. 157-171 (Year: 2014).*

(Continued)

*Primary Examiner* — Dominic Lazaro
(74) *Attorney, Agent, or Firm* — Sughrue Mion, PLLC

(57) ABSTRACT

A composition containing rose stem cell-derived exosomes as an active ingredient is provided for anti-inflammation, wound healing or wound healing acceleration. The composition has excellent effects on anti-inflammation, wound healing and/or wound healing acceleration.

9 Claims, 9 Drawing Sheets
(1 of 9 Drawing Sheet(s) Filed in Color)

Wound healing assay (6hr)

(56)            References Cited

FOREIGN PATENT DOCUMENTS

WO        2020/022731 A1     1/2020

OTHER PUBLICATIONS

Japanese Office Action dated Nov. 14, 2023 in Application No. 2022-565928.
"Cosmetic Ingredient", BIO-FD&C, Feb. 1, 2017, pp. 1-12.
International Search Report for PCT/KR2021/006189 dated Aug. 23, 2021 [PCT/ISA/210].
Extended European Search Report issued Mar. 11, 2024 in Application No. 21818610.4.
Sophie Rome, "Biological properties of plant-derived extracellular vesicles," Food Function, Royal Society of Chemistry, 2019, vol. 10, No. 2, pp. 529-538 (10 pages total).

* cited by examiner

Rose Callus Exosome

Wound healing assay (6hr)

COMPOSITION FOR ANTI-INFLAMMATION, WOUND HEALING OR WOUND HEALING PROMOTION, COMPRISING ROSE STEM CELL-DERIVED EXOSOMES AS ACTIVE INGREDIENT

CROSS REFERENCE

This application is a Bypass Continuation of International Application No. PCT/KR2021/006189 filed May 18, 2021, claiming priority based on Korean Patent Application No. 10-2020-0067466 filed Jun. 4, 2020 and Korean Patent Application No. 10-2021-0034311 filed Mar. 16, 2021, the entire contents of which are incorporated herein by reference.

TECHNICAL FIELD

The present invention relates to a composition for anti-inflammation, wound healing or wound healing acceleration comprising rose stem cell-derived exosomes as an active ingredient.

Moreover, the present invention relates to a method for preventing, suppressing, alleviating, ameliorating or treating inflammatory diseases, healing wound or accelerating wound healing using the aforesaid composition.

BACKGROUND ART

Inflammation is a defense response of the body against physical or chemical injury, infection of bacteria, fungi or viruses, or pathological conditions caused by various allergens and the like. Inflammatory response appears as part of innate immune response. Various substances and physiological and chemical phenomena are involved in inflammatory response, and recent studies have shown that various inflammatory cytokines play an important role in inflammatory response. Major cytokines involved in inflammatory response include IL-1B, TNF-α, IL-6, IL-8, IL-12, IFN-β, and the like. The increased expression and secretion of these cytokines and the activation thereof are associated with a series of complex physiological responses, including secretion of inflammatory mediators, immune cell infiltration, cell migration, and tissue destruction, as well as symptoms such as erythema, edema, fever and pain.

In general, inflammatory response does not become a significant problem and the affected area returns to its normal state, if the infectious agent is removed from the body and the damaged tissue is regenerated. However, if the infectious agent is not removed from the body or the inflammatory response is excessive or persistent due to internal substances of the body, acute or chronic inflammatory disease occurs. Non-steroidal anti-inflammatory drugs, steroidal anti-inflammatory drugs, antagonists of neuropeptides, COX inhibitors, anti-histamines, and immunosuppressive drugs such as cyclosporine A are used for alleviation or treatment of inflammatory response or inflammatory diseases caused thereby, but have problems that they cause adverse effects such as skin atrophy, vasodilation, depigmentation, hypersensitivity reactions, tolerance, neutropenia and the like. In addition, there is a limit that the aforesaid drugs merely help to control symptoms related to inflammation to a certain level rather than the underlying treatment therefor.

In recent years, studies have been actively conducted on the development of inflammatory disease therapeutics or functional cosmetics using natural substances. In the case of inflammatory disease therapeutics or functional cosmetics based on these natural substances, the amount of an active ingredient in the natural extract is low, and hence a large amount of the natural extract needs to be used to obtain the anti-inflammatory effect. In the majority of cases, the fact that these therapeutics or functional cosmetics are based on natural substances has been emphasized in marketing, but there is a need for more scientific research on the practical efficacies of natural substances on the anti-inflammatory effect. Further, functional cosmetics containing plant extracts as an active ingredient have problems that they may cause a foreign body sensation during their evaporation after topical application to the skin, and the duration of the effect thereof is short.

It is known that cells such as keratinocytes, fibroblasts, endothelial cells, macrophages and the like cooperate with each other in wound healing, and processes such as migration, proliferation and differentiation of these cells are regulated by various growth factors or cytokines. For this reason, wound healing methods using growth factors and cytokines have been developed.

However, the wound healing methods using growth factors and cytokines have problems that the wound healing time is long and one specific growth factor or cytokine does not exhibit a satisfactory therapeutic effect due to the wound healing mechanism through complex actions of involved several proteins. In addition, in view that mesenchymal stem cells secrete growth factors and cytokines, a method for healing wound using conditioned media of mesenchymal stem cells has been proposed. However, non-activated mesenchymal stem cells have a problem that the amount of cytokines and growth factors secreted from the cells is small. In addition, the conditioned media of mesenchymal stem cells also contain ingredients such as waste products secreted from the cells during cell growth, antibiotics added for contamination prevention, and animal-derived serum, etc. and thus when the conditioned media is applied to a wound, the wound is likely to be exposed to various risks.

Recently, there have been reports that cell secretomes contain various bioactive molecules that regulate cellular behaviors. In particular, cell secretomes contain 'exosome' or 'extracellular vesicle' that has intercellular signaling functions, and thus studies on the components and functions thereof have been actively conducted.

Cells shed various membranous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which comprises a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

That is, exosomes called "avatars" of cells contain bioactive factors such as growth factors, similar to cells, and serve as carriers that transmit bioactive factors between cells, that is, serve to mediate cell-to-cell communication. Exosomes are known to be released not only from animal cells such as stem cells, immune cells, fibroblasts and cancer cells, but also from cells of various organisms such as plants, bacteria, fungi, and algae. For example, exosomes may be isolated from conditioned media of plant stem cells, as well as conditioned media of cancer cells, immune cells, mesenchymal stem cells, and the like.

However, studies on the isolation, purification, and characterization of exosomes derived from plant stem cells remain insufficient. Therefore, more detailed characterization and functional studies of exosomes derived from plant stem cells are required.

Various varieties of roses are cultivated in a wide range of areas such as the cold, subarctic, temperate, and subtropical zones of the northern hemisphere, and extract thereof are used in perfumes and cosmetics. However, technologies to date are at a level where extracts obtained by drying rose petals and subjecting the dried petals to hot-water extraction or solvent extraction are used for perfumes and air fresheners.

In addition, a technology of using conditioned media of rose callus obtained by culturing rose callus has been introduced, but this technology is also merely at a level where conditioned media of callus themselves or extracts obtained by drying the callus and then subjecting the dried callus to hot-water extraction or solvent extraction are used as cosmetic ingredients. Further, conditioned media of rose callus contain growth regulators or a callus inducing substance, and thus are hardly regarded as natural cosmetic ingredients, and the growth regulators contained in the cultures may cause side effects such as skin troubles.

The present inventor has found that exosomes derived from rose stem cells are effective in anti-inflammation, wound healing or wound healing acceleration, and has developed a composition for anti-inflammation, wound healing or wound healing acceleration containing rose stem cell-derived exosomes as an active ingredient.

Meanwhile, it is to be understood that the matters described as the background art are intended merely to aid in the understanding of the background of the present invention and are not admitted as prior art against the present invention.

SUMMARY OF INVENTION

An object of the present invention is to provide a composition for anti-inflammation, wound healing or wound healing acceleration comprising rose stem cell-derived exosomes as an active ingredient.

Another object of the present invention is to provide a method for preventing, suppressing, alleviating, ameliorating or treating inflammatory diseases, healing wound or accelerating wound healing using the aforesaid composition.

However, the objects of the present invention as described above are illustrative and the scope of the present invention is not limited thereby. In addition, other objects and advantages of the present invention will be more apparent from the following description, the appended claims and the accompanying drawings.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF INVENTION

Figure 1A:
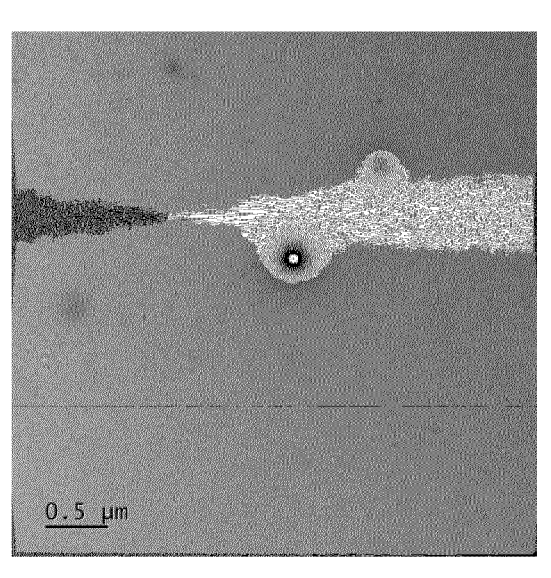
FIG. 1A shows particle images obtained by transmitted electron microscopy (TEM) of rose stem cell-derived exosomes obtained according to one embodiment of the present invention.
Figure 1A:
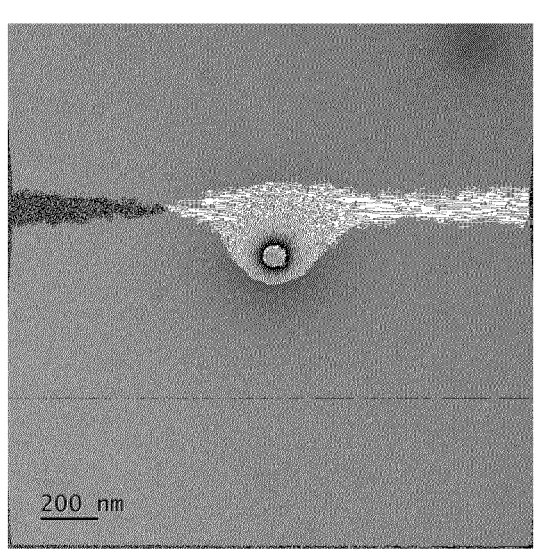
Figure 1A:
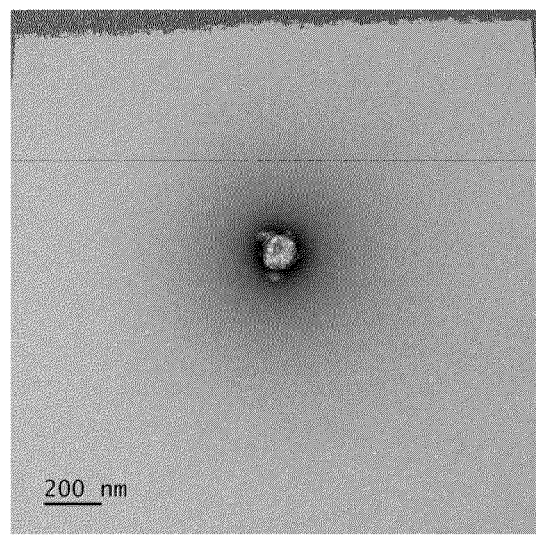
Figure 1A:
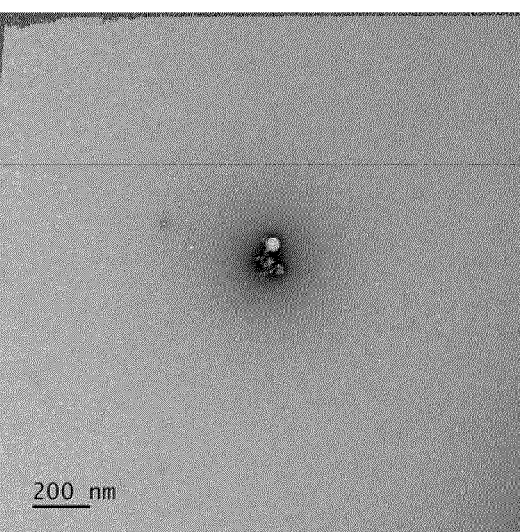

The present invention provides a composition for anti-inflammation, wound healing or wound healing acceleration containing rose stem cell-derived exosomes as an active ingredient.

As used herein, the term "rose (Rosa spp.)" refers to plants belonging to the genus Rosa, in the family Rosaceae, the order Rosales and the class Dicotyledoneae, and includes all of wild species and cultivated garden species.

As used herein, the term "exosomes" refers to nano-sized vesicles secreted or released from plant cells into extracellular spaces and having a membrane structure, and is also referred to as exosome-like vesicles or exosome-like particles.

As used herein, the term "anti-inflammation" means prevention, suppression, alleviation, amelioration or treatment of inflammation. As an example, not limiting the present invention, examples of the inflammatory diseases include dermatitis, atopic dermatitis, eczema, inflammation caused by bacterial, viral or fungal infections, burns, inflammation caused by burns, wounds, inflammation caused by wounds, and the like.

As used herein, the term "wound" means a condition in which a part or all of the body is injured, and is intended to encompass pathological conditions in which a tissue constituting an inside or an external surface of the body, for example, skin, muscle, nerve tissue, bone, soft tissue, internal organ, or blood vessel tissue, is damaged or destroyed. As an example, not limiting the present invention, examples of the wound include abrasion, laceration, stab wound, incised wound, avulsion, bedsore, tissue destruction caused by irradiation, penetrated wound, gunshot wound, burn, frostbite, surgical wound, sutures after plastic surgery, wound caused by chemical substance and so on, and may include any damage to any part of an individual.

As used herein, the term "iontophoresis" refers to a method of flowing a microcurrent through a skin to which an active ingredient has been applied, generating a potential difference thereby and changing the electrical environment of the skin, and thus allowing an ionized active ingredient to penetrate the skin by electrical repulsion. Examples of iontophoresis that is used in one embodiment of the present invention include: a method of introducing a microcurrent into a skin by allowing the microcurrent to flow from an external power source into an electrode patch on the skin, the microcurrent generated by the external power source; a method of introducing a microcurrent into a skin, the microcurrent generated by a battery provided in an electrode patch on the skin; and a method of introducing a microcurrent into a skin through a patch on the skin provided with a reverse electrodialysis device, the microcurrent generated by the concentration difference between high concentration electrolyte solution and low concentration electrolyte solution in the reverse electrodialysis device. However, the present invention is not limited thereto, and various types of iontophoresis may, of course, be used.

As used herein, the term "rose stem cell-derived exosomes" is meant to include all exosomes isolated from, for example, a conditioned medium of rose plant cells, a conditioned medium of rose callus, or a biological solution of rose equivalent thereto.

The composition containing rose stem cell-derived exosomes as an active ingredient according to one embodiment of the present invention may exhibit at least one effect selected from the group consisting of anti-inflammation, wound healing, and wound healing acceleration.

In the composition according to one embodiment of the present invention, the rose stem cells may be obtained by inducing a callus derived from rose embryos or leaves and then culturing cells of the callus.

For example, the composition containing rose stem cell-derived exosomes as an active ingredient according to the present invention may be a pharmaceutical composition for anti-inflammation, wound healing or wound healing acceleration. In addition, the composition containing rose stem cell-derived exosomes as an active ingredient according to the present invention may be used as a functional cosmetic composition, a skin external preparation or a quasi-drug for anti-inflammation, wound healing or wound healing acceleration.

As an example, not limiting the present invention, the composition according to one embodiment of the present invention may be administered or treated by injection, microneedling, iontophoresis, topical application, or a combination thereof. For example, the composition may be an injectable formulation, an infusion formulation, a spray formulation, a liquid formulation, or a patch formulation.

In one embodiment of the present invention, when the composition is used as a pharmaceutical composition, it may include pharmaceutically acceptable carriers, excipients or diluents. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. In addition, the effective amount of the pharmaceutical composition according to one embodiment of the present invention means the amount required for administration in order to achieve the effects of anti-inflammation, wound healing and/or wound healing acceleration.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the severity of disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

In addition, the present invention provides a method for treating inflammation, healing wound or accelerating wound healing, the method comprising administering a therapeutically effective amount of the composition to a mammal, or topically applying the composition to a skin, an inflammatory area, or a wounded area. The mammal may be at least one mammal selected from the group consisting of humans, dogs, cats, rodents, horses, cattle, monkeys and pigs.

The composition of the present invention is less likely to contain impurities such as growth regulation factors than conventional rose filtrates, rose extracts, conditioned media of rose callus, or filtrates or extracts thereof, and has excellent effects on anti-inflammation, wound healing and/or wound healing acceleration.

It should be understood that the scope of the present invention is not limited to the aforementioned effects.

EXAMPLES

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Preparation of Rose Stem Cells

According to preparation and culture methods of plant stem cells known in the art, calluses were induced from rose embryos and/or leaves, and cells of the induced callus were cultured. In addition, a callus having a good growth state was selected and cultured in large amounts, thereby preparing conditioned media of rose stem cells (conditioned media of rose callus).

Example 2: Preparation of Rose Stem Cell-Derived Exosomes

The conditioned media of rose stem cells (conditioned media of rose callus) prepared as described in Example 1 were purchased from BIO-FD&C Co., Ltd. (located in Incheon, Korea and supplying conditioned media of Damask Rose callus). The conditioned media of rose stem cells were filtered through a 0.22 μm filter to remove impurities such as cell debris, waste products and large particles. Rose stem cell-derived exosomes were isolated from the filtered conditioned media by tangential flow filtration (TFF) method.

Figure 1B:
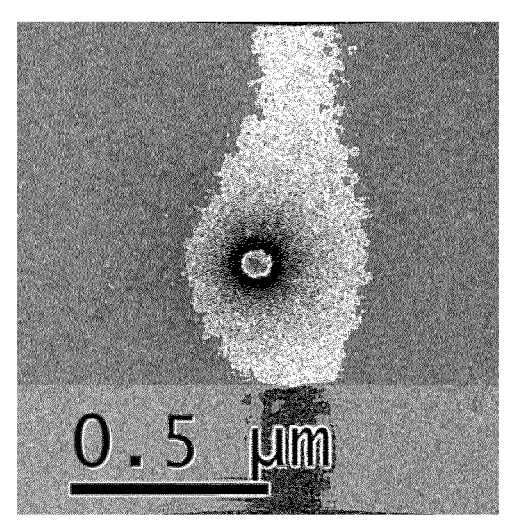
FIG. 1B shows enlarged particle images of FIG. 1A.
Figure 1B:
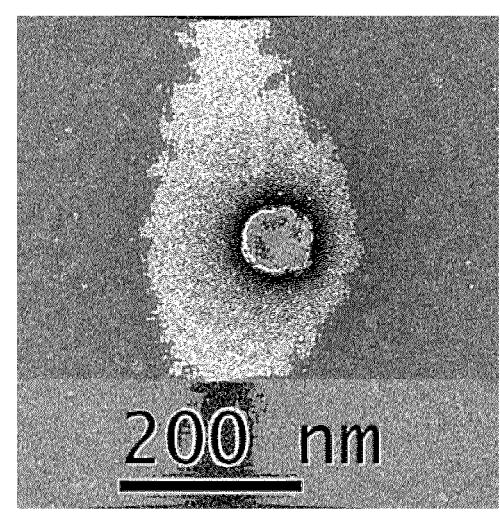
Figure 1B:
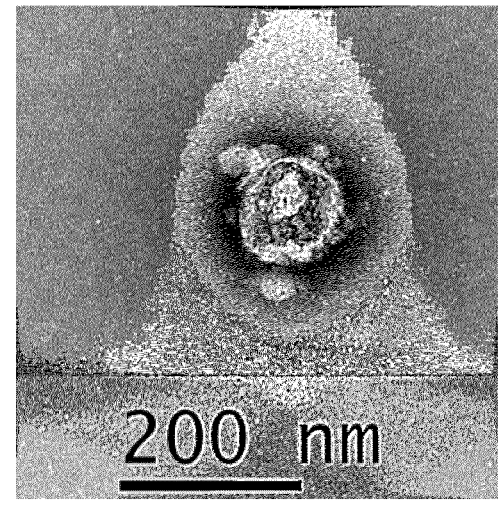
Figure 1B:
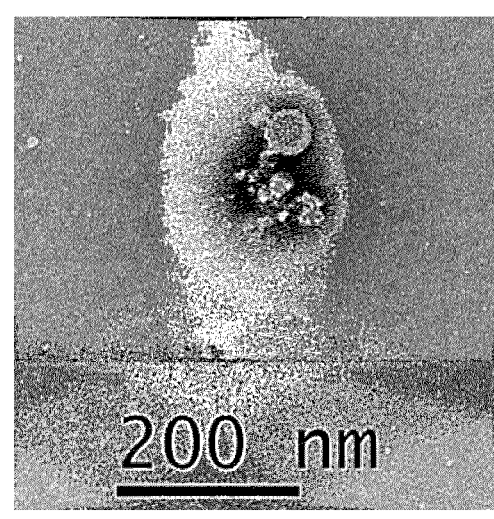
Figure 2:
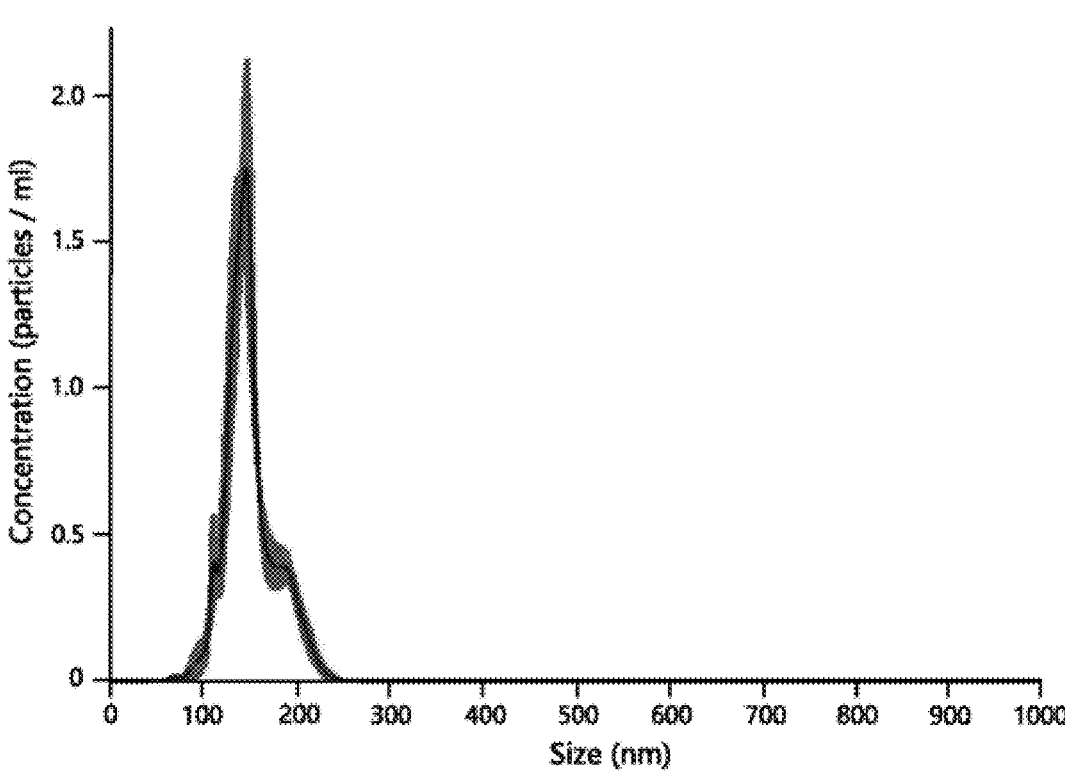
FIG. 2 is a graph showing the results of NTA analysis of rose stem cell-derived exosomes.

The size of the isolated rose stem cell-derived exosomes was analyzed by transmitted electron microscopy (TEM). As shown in FIGS. 1A and 1B, it was confirmed that the isolated rose stem cell-derived exosomes were nano-sized vesicles. The size and concentration of the rose stem cell-derived exosomes were analyzed by nanoparticle tracking analysis (NTA) using NS300 (purchased from Malvern Panalytical) (FIG. 2).

Figure 3:
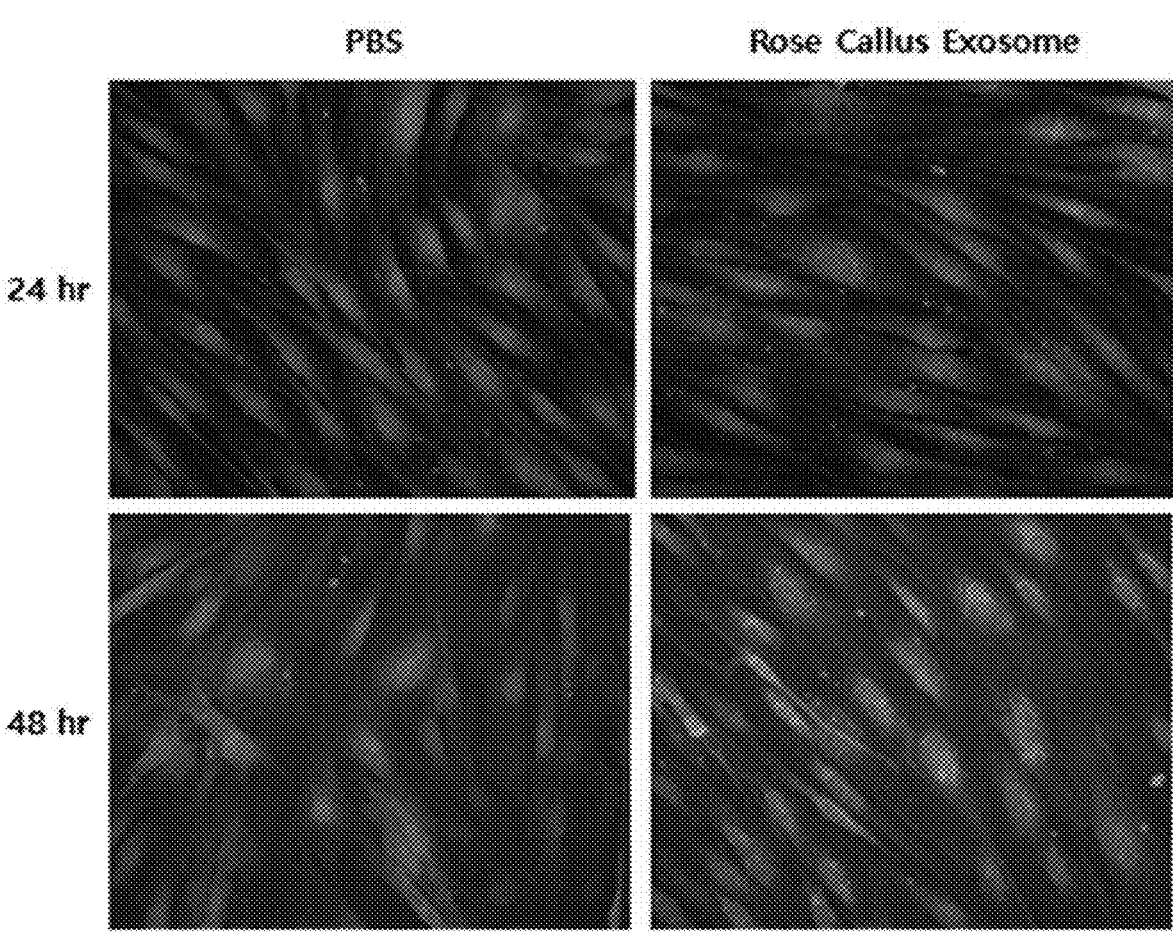
FIG. 3 depicts fluorescence microscopic images of cells showing that fluorescence-stained exosomes are delivered into human dermal fibroblasts (green: exosomes delivered into cells; blue: cell nucleus; and red: cell membrane).

Example 3: Evaluation of Delivery Ability of Rose Stem Cell-Derived Exosomes into Dermal Fibroblasts In order to examine whether the rose stem cell-derived exosomes would be delivered into human dermal fibroblasts (purchased from CEFO Co., Ltd.), the following analysis was performed. To fluorescence-stain the membrane of the rose stem cell-derived exosomes prepared in Example 2, the exosomes were allowed to react with PKH67 fluorescence dye (purchased from Sigma-Aldrich). After the reaction, the reaction solution was fractionated with an MW3000 column (purchased from ThermoFisher Scientific) to remove free PHK67 that was not stained in the exosome membrane. A negative control was prepared by allowing PKH67 fluorescence dye to react with a buffered solution and fractionating the reaction product with the MW3000 column. The exosomes stained with PKH67 were incubated with pre-cultured human dermal fibroblasts, and then whether the exosomes would be delivered into the cells over time was observed using a fluorescence microscope. Hoechst fluorescence dye (purchased from Sigma-Aldrich) was used to stain the cell nucleus, and CellMask Orange Plasma Membrane Stain fluorescence dye was used to stain the cell membrane. As a result of examining whether the exosomes would be delivered into the cells, it was confirmed that the fluorescence-stained exosomes were delivered into the cells and green fluorescence accumulated in the cells over time (FIG. 3).

Example 4: Evaluation of Skin Regeneration Effect Using Dermal Fibroblasts

To evaluate whether the rose stem cell-derived exosomes prepared as described in Example 2 promotes wound healing in human dermal fibroblasts, scratch-wound assay was performed. Human dermal fibroblasts dispersed in a DMEM containing fetal bovine serum were seeded into a culture plate for wound induction (ImageLock Plate; purchased from EssenBio) at a density of 10,000 cells/well and cultured for 24 hours under 5% $CO_2$ and 37° C. After the cells reached a confluency of 90% or more, scratches were made using a WoundMaker (purchased from EssenBio). To evaluate the skin regeneration effect using human dermal fibroblasts, experimental groups was classified as follows:
  (1) Negative control (NC): an experimental group treated with a serum-free medium alone;
  (2) Positive control (PC): an experimental group treated with a medium containing 10% fetal bovine serum;
  (3) Conditioned media of rose stem cells (CM): an experimental group treated with the conditioned media of rose stem cells (conditioned media of rose callus), which were prepared in Example 2 and diluted with a serum-free medium (treatment concentration of CM based on the number of particles: $1.0 \times 10^9$ particles/ mL); and
  (4) Rose stem cell-derived exosomes (EXO): an experimental group treated with the rose stem cell-derived exosomes, which were prepared in Example 2 and diluted with a serum-free medium (treatment concentration of EXO based on the number of particles: $1.0 \times 10^9$ particles/mL).

After that, each of the experimental groups was subjected to Scratch-Wound assay, and the human dermal fibroblasts were cultured at 37° C. under 5% $CO_2$ for 24 hours. At each of 6, 12 and 24 hours after the treatment of each experimental group, the wound healing efficacy in each experimental group was measured using Incucyte (purchased from Sartorius), respectively.

Figure 4A:
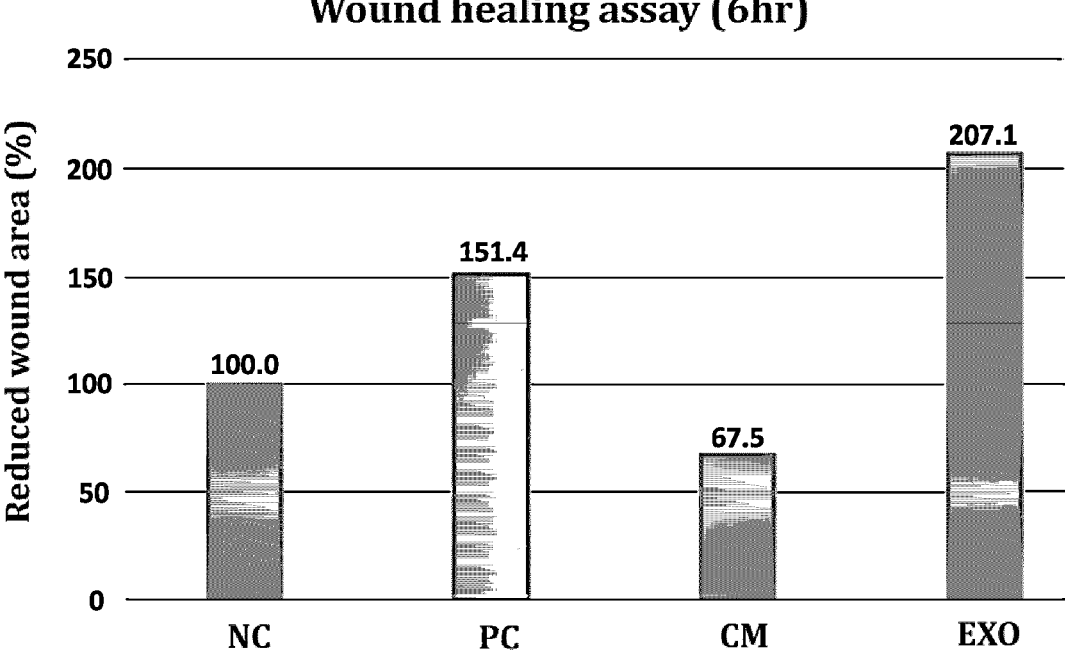
FIGS. 4A to 4C are graphs showing that the migration of human dermal fibroblasts remarkably increased after scratch-wounds of human dermal fibroblasts were treated with rose stem cell-derived exosomes.
Figure 4B:
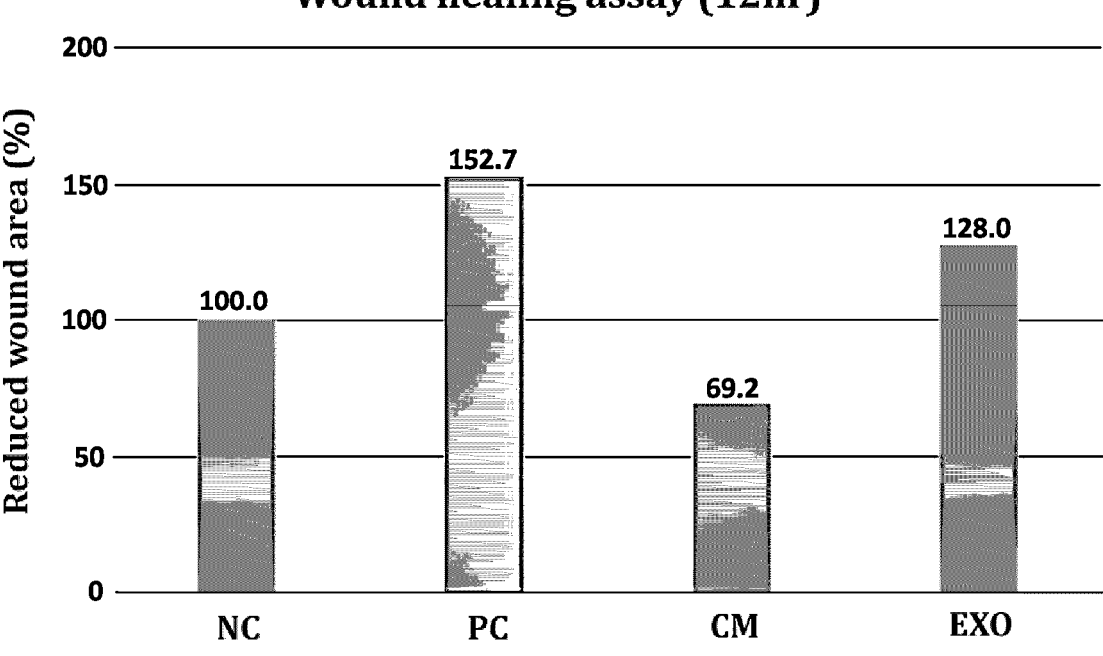
Figure 4C:
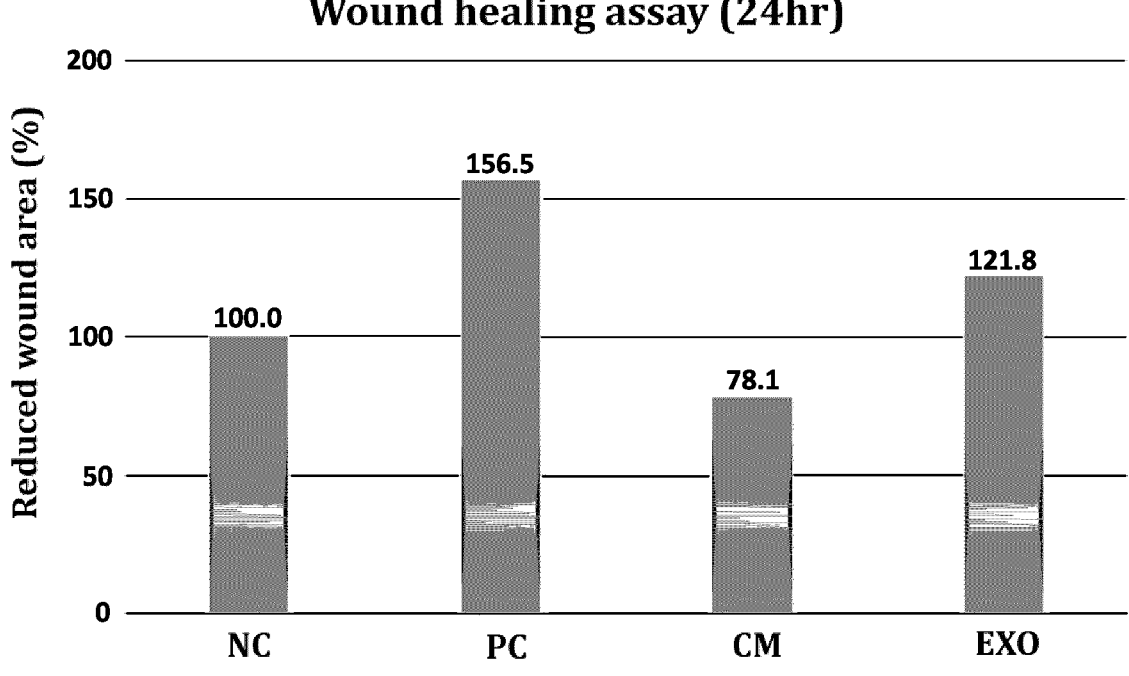

As a result of measuring the wound healing efficacy, it was confirmed that the treatment with the rose stem cell-derived exosomes of the present invention remarkably increased the migration of the human dermal fibroblast compared to the positive control at 6 hours after the treatment, and also remarkably increased the migration of the human dermal fibroblasts compared to the negative control and the conditioned media of rose stem cells at all the time points of measurement (at 6 hours, 12 hours and 24 hours after the treatment) (FIGS. 4A to 4C).

As can be seen from the above results, the rose stem cell-derived exosomes of the present invention have an excellent effect for promoting the migration of human dermal fibroblasts, that is, an excellent wound healing effect, as compared with the conditioned media of rose stem cells (conditioned media of rose callus).

Therefore, the rose stem cell-derived exosomes of the present invention are useful as an active ingredient of a composition for wound healing or wound healing acceleration.

Example 5. Evaluation 1 of Anti-Inflammatory Effect of Rose Stem Cell-Derived Exosomes To evaluate whether the rose stem cell-derived exosomes prepared as described in Example 2 exhibit an anti-inflammatory effect, RAW 264.7 cells were suspended in 10% FBS-containing DMEM, and then seeded into each well of a multi-well plate to reach a confluency of 80 to 90%. On the next day, the RAW 264.7 cells were treated for 24 hours with the rose stem cell-derived exosomes diluted in a LPS-containing fresh medium (DMEM containing 1% FBS and 200 nM LPS). Experimental groups for evaluation of the anti-inflammatory effect were classified as follows:
  (1) Negative control: an experimental group in which RAW 264.7 cells were treated with LPS alone;
  (2) Positive control (PC): an experimental group in which RAW 264.7 cells were treated with LPS plus 200 μM dexamethasone; and
  (3) Rose stem cell-derived exosomes (EXO): an experimental group in which RAW 264.7 cells were treated with the rose stem cell-derived exosomes, which were prepared in Example 2 and diluted with the LPS medium (treatment concentration of EXO based on the number of particles: $1.0 \times 10^9$ particles/mL).

After the completion of culturing the RAW 264.7 cells of each experimental group, the culture supernatant was collected, and the inflammatory response was checked by measuring the inflammatory cytokines present in the culture supernatant. The amount of inflammatory cytokines in the culture supernatant was measured using an IL-6 ELISA kit. The amount of IL-6 (inflammatory cytokine) produced in the group treated with LPS alone, and the amount of IL-6 (inflammatory cytokine) produced in the respective group treated with LPS plus each of dexamethasone and the rose stem cell-derived exosomes were measured using the ELISA kit (purchased from R&D system) according to the manufacturer's manual.

Figure 5:
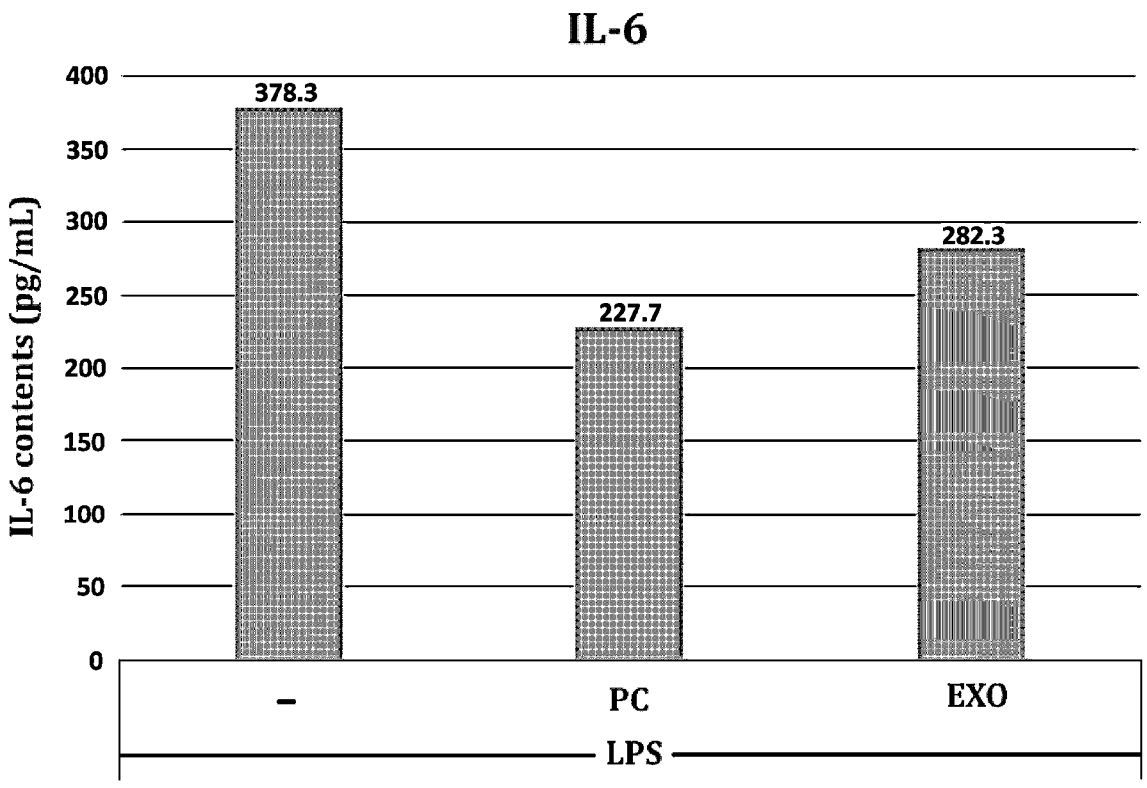
FIG. 5 is a graph showing that IL-6 induced in RAW 264.7 cells by LPS remarkably decreased when RAW 264.7 cells were treated with rose stem cell-derived exosomes.

As shown in FIG. 5, it was confirmed that, when RAW 264.7 cells, which are mouse macrophages, were treated with LPS plus the rose stem cell-derived exosomes of the present invention, the production of IL-6 was remarkably inhibited compared to that in the negative control group in which the RAW 264.7 cells were treated with LPS alone, and the production of IL-6 decreased to a level similar to that in the positive control group in which RAW 264.7 cells were treated with LPS plus dexamethasone.

As can be seen from the above results, the rose stem cell-derived exosomes of the present invention have an excellent anti-inflammatory effect. Thus, the rose stem cell-derived exosomes of the present invention are useful for preventing, suppressing, alleviating, ameliorating or treating inflammatory diseases.

Example 6. Evaluation 2 of Anti-Inflammatory Effect of Rose Stem Cell-Derived Exosomes To evaluate whether the rose stem cell-derived exosomes prepared as described in Example 2 exhibit an anti-inflammatory effect, RAW 264.7 cells were suspended in 10% FBS-containing DMEM, and then seeded into each well of a multiwell plate to reach a confluency of 80 to 90%. On the next day, the RAW 264.7 cells were treated for 24 hours with the rose stem cell-derived exosomes diluted in a LPS-containing fresh medium (DMEM containing 1% FBS and 200 nM LPS). Experimental groups for evaluation of the anti-inflammatory effect were classified as follows:

(1) Negative control (NC): an experimental group in which RAW 264.7 cells were treated with LPS alone;

(2) Positive control (PC): an experimental group in which RAW 264.7 cells were treated with LPS plus 200 μM dexamethasone;

(3) Conditioned media of rose stem cells (CM): an experimental group in which RAW 264.7 cells were treated with the conditioned media of rose stem cells (conditioned media of rose callus), which were prepared in Example 2 and diluted with the LPS medium (treatment concentration of CM based on the protein content: 5 μg/mL, and 50 μg/mL); and (4) Rose stem cell-derived exosomes (EXO): an experimental group in which RAW 264.7 cells were treated with the rose stem cell-derived exosomes, which were prepared in Example 2 and diluted with the LPS medium (treatment concentration of EXO based on the protein content: 5 μg/mL, and 50 μg/mL).

After the completion of culturing the RAW 264.7 cells of each experimental group, the culture supernatant was collected, and the inflammatory response was checked by measuring the inflammatory cytokines present in the culture supernatant. The amount of inflammatory cytokines in the culture supernatant was measured using an IL-6 ELISA kit (purchased from R&D system). The amount of IL-6 (inflammatory cytokine) produced in the group treated with LPS alone, and the amount of IL-6 (inflammatory cytokine) produced in the respective group treated with LPS plus each of dexamethasone, the conditioned media of rose stem cells (conditioned media of rose callus) and the rose stem cell-derived exosomes were measured using the ELISA kit according to the manufacturer's manual. The remaining cells were subjected to cell viability measurement using MTT assay (purchased from Sigma-Aldrich), and the measured values of IL-6 were normalized using the cell viability.

Figure 6:
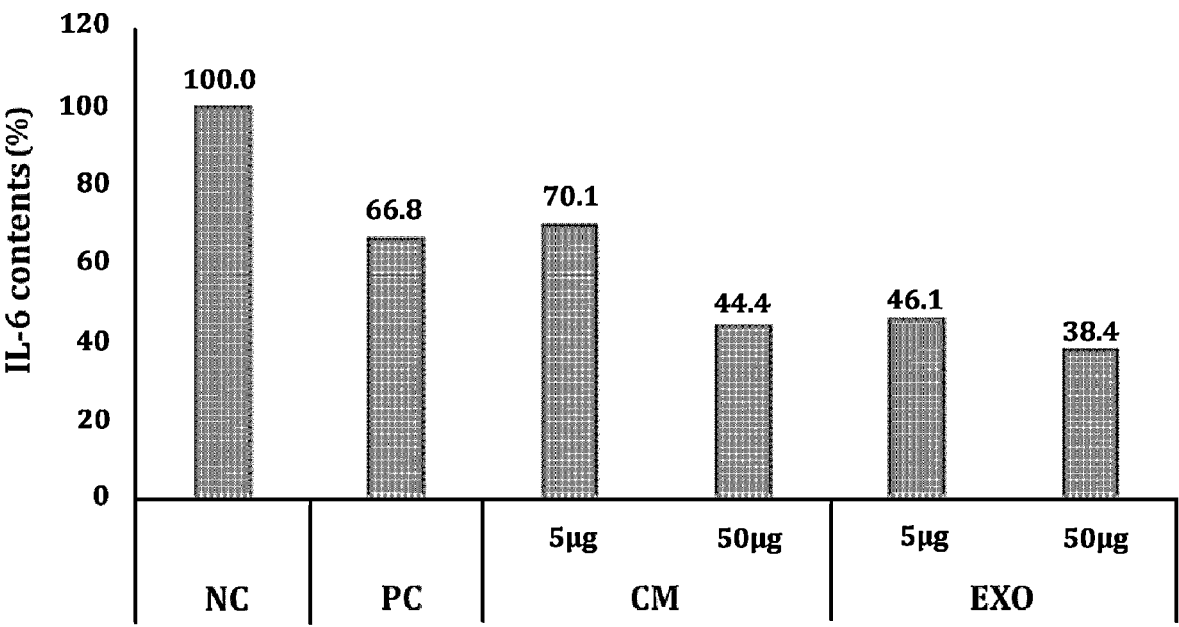
FIG. 6 is a graph showing that rose stem cell-derived exosomes have an excellent effect of reducing IL-6 (inflammatory cytokine), i.e., an excellent anti-inflammatory effect, as compared with conditioned media of rose stem cells (conditioned media of rose callus).

As shown in FIG. 6, it was confirmed that, when RAW 264.7 cells, which are mouse macrophages, were treated with LPS plus the rose stem cell-derived exosomes of the present invention, the production of IL-6 was remarkably inhibited compared to that in the negative control group in which RAW 264.7 cells were treated with LPS alone, and the production of IL-6 also decreased to a level superior to that in the positive control group in which RAW 264.7 cells were treated with LPS plus dexamethasone.

In addition, it was confirmed that, when RAW 264.7 cells were treated with LPS plus the rose stem cell-derived exosomes of the present invention, the production of IL-6 decreased to a level superior to that in the CM group in which RAW 264.7 cells were treated with LPS plus the same concentration of the conditioned media of rose stem cells (conditioned media of rose callus). In particular, it was confirmed that, when RAW 264.7 cells were treated with LPS plus the rose stem cell-derived exosomes of the present invention at a concentration of 5 μg/mL, the production of IL-6 was remarkably inhibited, as compared with the CM group in which RAW 264.7 cells were treated with LPS plus the same concentration of the conditioned media of rose stem cells (conditioned media of rose callus).

As can be seen from the above results, the rose stem cell-derived exosomes of the present invention have an excellent anti-inflammatory effect, as compared with the conditioned media of rose stem cells (conditioned media of rose callus). Thus, the rose stem cell-derived exosomes of the present invention are useful for preventing, suppressing, alleviating, ameliorating or treating inflammatory diseases.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

I claim:

1. A method for reducing a level of interleukin-6 (IL-6) thereby suppressing, alleviating, ameliorating or treating dermatitis, atopic dermatitis, eczema, inflammation caused by infections, and inflammation caused by wounds in a subject in need thereof, the method comprising administering an anti-inflammatory composition to an area of skin of the subject, wherein said area of the skin is affected by dermatitis, atopic dermatitis, eczema, inflammation caused by infections, or inflammation caused by wounds, wherein the anti-inflammatory composition comprises exosomes derived from rose stem cells as an active ingredient, and wherein the exosomes are isolated from a conditioned medium of the rose stem cells.

2. The method of claim 1, wherein the anti-inflammatory composition is administered to the area of the skin of the subject by injection, microneedling, iontophoresis, or a combination thereof.

3. The method of claim 1, wherein the anti-inflammatory composition is an injectable formulation, an infusion formulation, a spray formulation, a liquid formulation, or a patch formulation.

4. The method of claim 1, wherein the rose stem cells are obtained by inducing a callus from rose embryos or leaves and then culturing cells of the callus.

5. The method of claim 1, wherein the subject is at least one selected from the group consisting of humans, dogs, cats, rodents, horses, cattle, monkeys and pigs.

6. A method for reducing a level of IL-6 thereby suppressing, alleviating, ameliorating or treating dermatitis, atopic dermatitis, eczema, inflammation caused by infections, and inflammation caused by wounds in a subject in need thereof, the method comprising topically applying an anti-inflammatory composition to an area of skin of the subject, wherein said area of the skin is affected by dermatitis, atopic dermatitis, eczema, inflammation caused by infections, or inflammation caused by wounds, wherein the anti-inflammatory composition comprises exosomes derived from rose stem cells as an active ingredient, and wherein the exosomes are isolated from a conditioned medium of the rose stem cells.

7. The method of claim 6, wherein the anti-inflammatory composition is a spray formulation, a liquid formulation, or a patch formulation.

8. The method of claim 6, wherein the rose stem cells are obtained by inducing a callus from rose embryos or leaves and then culturing cells of the callus.

9. The method of claim 6, wherein the subject is at least one selected from the group consisting of humans, dogs, cats, rodents, horses, cattle, monkeys and pigs.

* * * * *